United States Patent [19]

Beasley et al.

[11] Patent Number: 5,736,549
[45] Date of Patent: Apr. 7, 1998

[54] HYPOXANTHINE AND GUANINE COMPOUNDS

[75] Inventors: Steven Colin Beasley; Alan Findlay Haughan; John Montana; Robert John Watson, all of Cambridge, United Kingdom

[73] Assignee: Chiroscience Limited, Cambridge, United Kingdom

[21] Appl. No.: 539,568

[22] Filed: Oct. 5, 1995

[30] Foreign Application Priority Data

Oct. 5, 1994 [GB] United Kingdom .............. 9420045
Oct. 5, 1994 [GB] United Kingdom .............. 9420093
Oct. 5, 1994 [GB] United Kingdom .............. 9420127

[51] Int. Cl.[6] .................... C07D 473/18; C07D 473/30; A61K 31/52
[52] U.S. Cl. .................... 514/262; 544/265; 544/276; 544/277
[58] Field of Search .................... 544/265, 276, 544/277; 514/262

[56] References Cited

U.S. PATENT DOCUMENTS

| | | | |
|---|---|---|---|
| 4,241,063 | 12/1980 | Naito et al. | 544/277 |
| 5,314,893 | 5/1994 | Tino et al. | 536/23 |

FOREIGN PATENT DOCUMENTS

| | | |
|---|---|---|
| 0156559 | 10/1985 | European Pat. Off. . |
| 156559 | 10/1985 | European Pat. Off. . |
| 0178178 | 4/1986 | European Pat. Off. . |
| 178178 | 4/1986 | European Pat. Off. . |
| 0193454 | 9/1986 | European Pat. Off. . |
| 193454 | 9/1986 | European Pat. Off. . |
| 0260491 | 3/1988 | European Pat. Off. . |
| 260491 | 3/1988 | European Pat. Off. . |
| 0302644 | 2/1989 | European Pat. Off. . |
| 302644 | 2/1989 | European Pat. Off. . |
| 0334361 | 9/1989 | European Pat. Off. . |
| 334361 | 9/1989 | European Pat. Off. . |
| 87-05604 | 8/1987 | WIPO . |
| 8705604 | 9/1987 | WIPO . |
| 91-06548 | 5/1991 | WIPO . |
| 9106548 | 5/1991 | WIPO . |
| 93-25565 | 12/1993 | WIPO . |
| 9325565 | 12/1993 | WIPO . |
| 95-22330 | 8/1995 | WIPO . |

*Primary Examiner*—Mark L. Berch
*Attorney, Agent, or Firm*—Saliwanchik, Lloyd & Saliwanchik

[57] ABSTRACT

Compounds of formula I

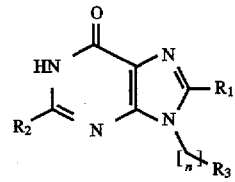

where
n=0-2;
$R^1$ is H, $NH_2$ or a halogen;
$R^2$ is H or $NH_2$;
$R^3$ is any of the four groups

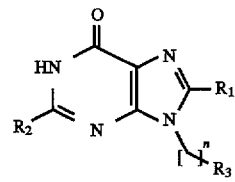

(I)

where
m=0 or 1; and
X is O, $NR^5$, or $S(O)_{0-2}$ and, in group (b), the X's may be the same or different.

Compounds of the invention have utility as inhibitors of purine nucleoside phosphyorylase (PNP).

17 Claims, No Drawings

HYPOXANTHINE AND GUANINE COMPOUNDS

FIELD OF THE INVENTION

The invention relates to purine and guanine derivatives which are particularly potent purine nucleoside phosphorylase (PNP) inhibitors, methods for preparation thereof, pharmaceutical compositions comprising said compounds, and their use in inhibiting purine nucleoside phosphorylase and for treating conditions in mammals which are responsive to purine nucleoside phosphorylase inhibition.

BACKGROUND OF THE INVENTION

9-Arylmethyl-substituted purines (including guanines) have been reported as PNP inhibitors in European patent application 178,178 substantially corresponding to U.S. Pat. No. 4,772,606; 9-arylmethyl-substituted purines (including guanines), in which the aryl ring contains phosphonic acid groups, have also been reported as PNP inhibitors in European patent application 465,297 and WO 92/05180. Modified purines, namely 9-deazapurines, have also been reported as PNP inhibitors in the U.S. patents U.S. Pat. No. 4,985,434; U.S. Pat. No. 5,008,265; U.S. Pat. No. 4,985,433; U.S. Pat. No. 5,236,926; U.S. Pat. No. 5,236,926 and U.S. Pat. No. 5,008,270.

PNP inhibitory data cited in Drugs of the Future, 13,654 (1988), Agents and Actions, 21,253 (1987), Prof Natl Acad Sci USA, 88, 11540 (1991) and WO 90/01021 indicate that modifications to the guanine base markedly alter the PNP-inhibitory ability of such compounds. Also, modifications to the aryl ring of the 9-deaza (9-arylmethyl) purines can markedly alter PNP inhibitory activity. Namely replacement of a pyridine ring with piperidine greatly reduces activity as illustrated in IL Farmaco, 48 (2), 297 (1993).

SUMMARY OF THE INVENTION

The present invention relates to the compounds of formula (I)

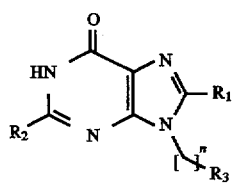

wherein:

n=0–2

$R^1$ is H, $NH_2$ or halogen;

$R^2$ is H or $NH_2$;

$R^3$ is any of the four groups;

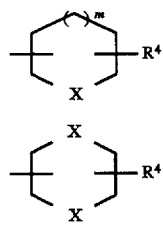

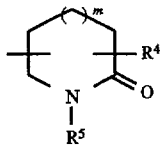

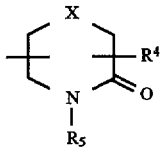

where m=0 or 1;

X is O, $NR^5$ or $S(O)_{0-2}$ and, in group (b), the X's may be the same or different;

$R^4$ is H or one or more groups independently selected from $C_{1-6}$ alkyl-$R^6$ and aryl-$R^6$;

$R^5$ is H, $C_{1-6}$ alkyl-$R^6$, $C_{2-6}$ alkenyl, aryl, -aryl-$C_{1-6}$ alkyl, —$C_{1-6}$ alkyl-aryl, —$C_{1-6}$ alkyl-hetero ($C_{1-6}$) alkyl, $CO_2$—$C_{1-6}$ alkyl-$R^6$, CONH—$C_{1-6}$ alkyl-$R^6$, CO—$C_{1-6}$ alkyl-$R^6$ or $SO_2$—$C_{1-6}$ alkyl-$R^6$; and $R^6$ is H, $CO_2H$, $CO_2C_{1-6}$ alkyl, $CONH_2$, $CON(C_{1-6}$ alkyl)$_2$, $CONH(C_{1-6}$ alkyl), CO—$C_{1-6}$ alkyl, CO-aryl, CO-heteroaryl, tetrazolyl, $NHSO_2CF_3$, $SO_2NH$—$C_{1-6}$ alkyl, $SO_2N(C_{1-6}$ alkyl)$_2$, $SO_2NH$-aryl, NHCO—$C_{1-6}$ alkyl, NHCONH—$C_{1-6}$ alkyl, NHCONH-aryl, $NHSO_2$—$C_{1-6}$ alkyl, $NHSO_2$-aryl, CN, $NH_2$, OH, O—$C_{1-6}$ alkyl or O-aryl;

in any tautomeric, salt, solvate and/or hydrate form.

The compounds of the invention are particularly useful in mammals as purine nucleoside phosphorylase (PNP) inhibitors, as selective inhibitors of T-cells and for suppressing cellular immunity. They can thus be used for the treatment of autoimmune diseases, transplant rejection, psoriasis or gout in mammals. They can also be used to potentiate the antiviral and antitumor effect of antiviral or antitumor purine nucleosides.

DESCRIPTION OF THE INVENTION

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric centre to represent the possibility of R- and S- configurations, and the < line and the . . . line to represent a unique configuration at an asymmetric centre. As used in this specification, alone or in combination, the term "$C_{1-6}$ alkyl" refers to a straight or branched chain alkyl moiety having from one to six carbon atoms, including for example, methyl, ethyl, propyl, isopropyl, butyl, t-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "aryl" means an optionally substituted phenyl or napthyl group with the substituent(s) being selected, for example, from halogen, trifluoromethyl, $C_{1-6}$ alkyl, phenyl and the like. The term "halogen" means fluorine, chlorine, bromine or iodine.

The term "hetero" means oxygen, sulphur (all possible oxidation states) or nitrogen optionally substituted with H or $C_{1-6}$ alkyl.

The term "heteroaryl" means an aromatic system comprising 5–10 atoms of which at least one atom is from the group O, S or N.

The term "cycloalkyl" means a saturated ring comprising of 3–9 carbon atoms, and "substituted cycloalkyl" means a cycloalkyl ring optionally substituted with substituents being selected, for example, from halogen, trifluouromethyl, $C_{1-6}$ alkyl, phenyl and the like.

Salts of compounds of formula (I) include pharmaceutically acceptable salts, for -example acid addition salts derived from inorganic or organic acids, such as hydrochlorides, hydrobromides, hydroiodides, p-toluenesulphonates, phosphates, sulphates, perchlorates, acetates, trifluoroacetates, propionates, citrates, malonates, succinates, lactates, oxalates, tartrates and benzoates. Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As part of the current invention, any group of compounds in which an ester function (e.g. when $R^5$ is $CO_2$—$C_{1-6}$ alkyl-$R^6$) is present, that ester may take the form of a metabolically labile ester in which the alcohol portion constitutes, for example, an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl,2-methyl-1-propionyloxypropyl, 2,4,6-trimethylbenzyloxymethyl or pivaloyloxymethyl group.

It will also be recognised by those skilled in the art that guanines of formula (I) can exist in the tautomeric forms depicted below.

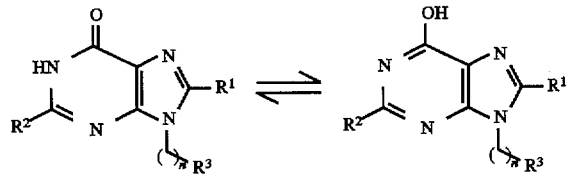

Preferred compounds of the invention include those in which, independently or in any combination:

n=1;

$R^1$ is $NH_2$ or halogen;

$R^2$ is $NH_2$;

$R^3$ is any of groups a), b) or c), and X is O, S or $NR^5$;

$R^4$ is H or $C_{1-6}$ alkyl-$R^6$;

$R^5$ is $C_{1-6}$ alkyl-$R^6$; and $R^6$ is H, $CO_2H$, $CO_2$-$C_{1-6}$ alkyl, OH, $NH_2$, tetrazolyl or $NHSO_2CF_3$.

Preferred compounds include the salts, solvates and hydrates of such compounds. In each of the cases a) or b) or c) compounds include all possible substitution patterns of $R^4$ around the rings and many also include $R^4$ substitution at more than one position on the ring.

The compounds of the invention are particularly useful for selectively suppressing T-cell mediated immunity in mammals, and for treating conditions in mammals in which T-cells are involved; these include but are not restricted to autoimmune diseases, transplant rejection, psoriasis or gout. Disorders considered to be of autoimmune origin include, but are not restricted to, rheumatoid arthritis, systemic lupus erythematosus, myasthenia gravis, type I diabetes and multiple sclerosis.

The compounds of the invention are also useful for inhibiting the in vivo metabolic degradation of purine nucleosides via phosphorolysis and are thus useful to potentiate the antiviral and antitumor efficacy of 2' and/or 3'-mono- or dideoxy purine nucleosides. For instance, may be useful for potentiating e.g. 2',3'-dideoxyadenosine, 2'3'-dideoxyguanosine or 2',3'-dideoxyinosine for the treatment of retrovirus infections such as acquired immunodeficiency syndrome (AIDS). They may also useful for potentiating the antitumor/cytotoxic effect of e.g. 2'-deoxyguanosine in mammals.

The compounds of the invention are also useful for the treatment of parasitic disorders in which the parasite uses PNP to generate its own DNA constituents (ie the purine bases). Inhibition of the parasite PNP by compounds of the present invention in, for example malaria, causes death of the parasite.

The above-cited properties are demonstrable in in vitro and in vivo tests using advantageously mammals, e.g. rats, mice, dogs, calves, and isolated cells thereof. Said compounds can be applied in vitro in the form of solutions, e.g. preferably aqueous solutions and in vivo either enterally or parenterally, advantageously orally and intravenously. The dosage in vitro may range between about $10^{-5}$ and $10^{-8}$ molar concentrations. The dosage in vivo may range, depending on the route of administration, between about 0.01 and 50 mg/kg.

PNP inhibition may be measured radiochemically by measuring the formation of $^{14}C$-guanine from $^{14}C$-guainosine using a modification of the method employed previously (J. C. Sircar et al J. Med. Chem. 29 1804 (1986)) employing calf spleen as the enzyme source and 1 mM phosphate. Results are expressed as $IC_{50}$ values, corresponding to the concentration of compound required to achieve a 50% reduction of the formation of guanine.

The potentiation of the cell growth inhibitory activity (cytotoxicity) of 2'-deoxyguanosine (d-Guo) by the compounds of the invention is determined as follows: MOLT-4 cells are grown in RPMI-1640 medium. To suspension cultures of these cells, d-Guo at a fixed concentration of (10 mM) and the candidate PNP inhibitor at varied concentrations are added. The degree of cell proliferation is measured by addition of $^3H$-Thymidine for the final 16 hours of a total culture period of 72 hours. The level of incorporation of $^3H$-Thymidine is assessed by liquid scintillation spectrometry. From this dam, the $IC_{50}$ is calculated as the concentration of PNP inhibitor required to reduce the incorporation of $^3H$-Thymidine to 50% of that of control cultures. This method is similar to that used previously to determine the effectiveness of PNP inhibitors on the potentiation of the toxicity of d-Guo (I. S. Kazmers, Science, 24, 1137–1139 (1981)); and other references. PNP inhibition can also be determined in vivo essentially as described in Agents and Actions, 22, 379 (1987) by measuring compound induced increase in plasma inosine levels in the rat.

Demonstration of the efficacy of compounds of formula I in an in vivo model of a T-cell mediated disease may be carried out by using the Dinitrofluorobenzene (DNFB) sensitised mouse model of contact dermatitis. DNFB is applied topically to young adult female Balb/c mice on days 1 and 2 in a suitable vehicle. On day 6 the animals may be challenged by application of DNFB to one ear. Compounds of the invention may be dosed by an appropriate route in an appropriate vehicle. Determination of efficacy may be carried out in a number of ways, an example of which is measurement of ear thickness using calipers. Results are expressed as percentage reduction in inflammatory response. This method is similar to that reported in WO94/23309.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a particular stereoisomer of formula (I) is required, the synthetic processes described herein may be used with the appropriate homochrial starting material and/or isomers may be resolved from mixtures using conventional separation techniques (e.g. hplc).

The compounds according to the invention may be prepared by the following processes. In the description and the formulae below the groups $R^1$, $R^2$, $R^3$, $R^4$, $R^5$, $R^6$, X, n, m and p are as defined above, except where otherwise stated. It will be appreciated that functional groups, such as amino, hydroxyl or carboxyl groups, present in the various compounds described below, and which it is desired to retain, may need to be in a protected form before any reaction is initiated. In such instances, removal of the protecting group may be the final step in a particular reaction. Suitable protecting groups for such functionality will be apparent to those skilled in the art. For specific details see "Protective Groups in the Organic Synthesis", Wiley Interscience, T. W. Greene, P. G. M. Wutts. Thus the processes required for preparing compounds of general formula (I) where $R^1=NH_2$ comprise:

deprotecting a compound of general formula (II)

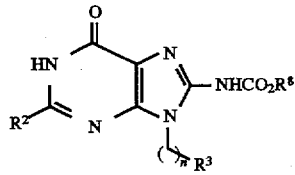

(II)

wherein $R^8$ represents a suitably labile group such as an alkyl group, e.g. ethyl, or an arylalkyl group, e.g. benzyl.

The deprotection reaction may be performed using standard conditions for hydrolysis reactions of this type. Thus, for example the reaction may be achieved in a solvent such as water containing an inert organic solvent such as an ether, e.g. a cyclic ether such as tetrahydrofuran, an amide, e.g. a substituted amide, such as dimethylformamide, or an alcohol, e.g. ethanol, in the presence of an inorganic base such as potassium carbonate or sodium hydroxide, at a temperature ranging from room temperature to the reflux temperature of the solvent mixture, preferably the reflux temperature of the solvent mixture.

Alternatively, when $R^8$ contains groups that are labile to hydrogenation, this may be performed as a method of deprotection. Thus, for example the reaction may be achieved in an inert solvent such as an alcohol, e.g. ethanol, in the presence of a transition metal catalyst, e.g. palladium on carbon, at a low temperature, preferably room temperature.

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I).

Intermediates of general formula (II) may be prepared by rearrangement of compounds of intermediate (III)

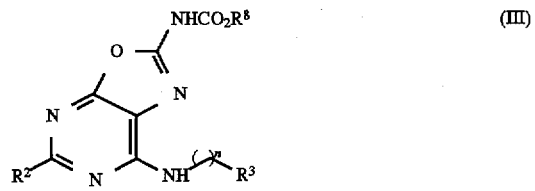

(III)

The rearrangement reaction may be performed using standard conditions for this reaction as outlined by J. Wang et al., J. Org. Chem., 53, 5617 (1988): Thus, for example the reaction may be achieved in a solvent, for example an inert organic solvent such as an ether, e.g. a cyclic ether such as tetrahydrofuran, an amide, e.g. a substituted amide such as dimethylformamide, or an alcohol such as ethanol at a temperature ranging from ambient temperature to the reflux temperature of the solvent, preferably the reflux temperature of the desired solvent, in the presence of an inorganic base such as potassium carbonate or sodium methoxide.

Intermediates of general formula (III) may be prepared from thioureas of general formula (IV)

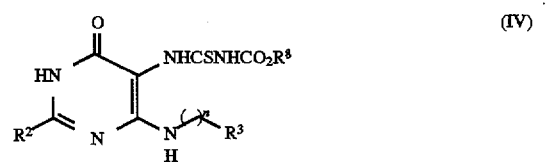

(IV)

This transformation may be performed using the procedure outlined by J. Wang et al., J. Org. Chem., 53, 5617 (1988). Thus, for example the reaction may be undertaken in the presence of an inert organic solvent such as an ether, e.g. a cyclic ether such as tetrahydrofuran, an amide e.g. a substituted amide such as dimethylformamide, or a nitrile such as acetonitrile, at ambient temperature, preferably 20°–30° C., in the presence of a diimide, e.g. dicyclohexylcarbodiimide. It is also an aspect of the present invention that intermediates of formula (II) may be prepared from intermediates of formula (IV) by combining the above documented procedures in one step.

Thioureas of general formula (IV) may be prepared from amines of general formula (V)

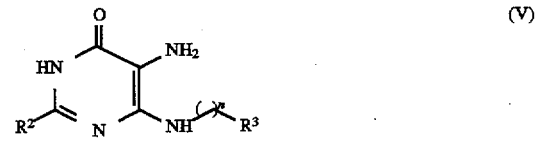

(V)

and isothiocyanates of general formula (VI)

$S=C=NCO_2R^8$ (VI)

This transformation may be performed using the procedure outlined by J. Wang et al., J. Org. Chem., 53, 5617 (1988). Thus, for example the reaction may be undertaken in the presence of an inert organic solvent such as an ether, e.g. a cyclic ether such as tetrahydrofuran, a nitrile such as acetonitrile or a halogenated hydrocarbon such as dichloromethane, at a low temperature, preferably ambient temperature, optionally in the presence of a base, e.g. an organic base such as an amine, e.g. triethylamine.

The thioureas of general formula (VI) may be prepared by the general procedure of J. Wang et al., J. Org. Chem., 53, 5617 (1988).

The amines of general formula (V) may be prepared by reduction of nitro derivatives of general formula (VII)

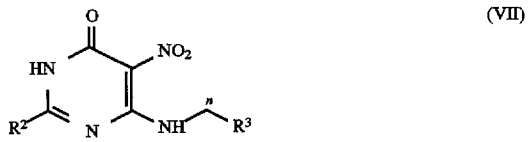
(VII)

It will be appreciated by those skilled in the art, that reduction reactions of this type can be affected by several methods as outlined in Advanced Organic Chemistry (4th edition), J. March, Wiley Interscience, p1216–1218. A non-limiting example of this transformation would involve the use of water as solvent, optionally in the presence of an inert organic solvent such as an ether, e.g. a cyclic ether such as tetrahydrofuran or an amide, e.g. a substituted amide such as dimethylformamide, in the presence of sodium dithionite at elevated temperature, preferably 65°–80° C.

The nitro derivatives of general formula (VII) may be prepared by reaction of the pyrimidinones of general formula (VIII)

(VIII)

with amines of general formula (IX)

(IX)

This reaction may be performed using standard conditions as envisaged by those skilled in the art. Thus, for example the reaction may be achieved in a solvent, for example an inert organic solvent such as ether, e.g. a cyclic ether such as tetrahydrofuran, an amide e.g. a substituted amide such as dimethylformamide or an alcohol such as ethanol, at a high temperature, preferably the boiling point of the solvent, in the presence of a base, e.g. an organic base such as an amine, e.g. triethylamine or a cyclic amine such as N-methylmorpholine.

The preparation of the nitro derivatives (VIII) are documented in C. Temple et at., Nucleic Acid Chemistry, Volume (I) (1978), Wiley New York, Eds L. B. Townsend et al., p47–52.

As a further extension of the invention intermediates of formula (V) can also be prepared from pyrimidines of formula (X), by reaction with reagents known to those skilled in art for the introduction of nitrogen substitution.

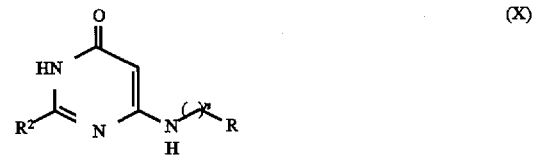
(X)

Thus the reaction may be performed using standard conditions for amination reactions of this type. Thus, for example the reaction may be achieved in a solvent, for example water or an organic acid such as acetic acid or aqueous mixtures thereof, in the presence of sodium nitrite, at a low temperature, e.g. 0° C. to ambient temperature, such as 10° C. to ambient temperature. After work up procedures evident to those skilled in the art, the residue may be dissolved in a suitable solvent such as water, optionally in the presence of a cosolvent, for example an inert organic solvent such as an ether, e.g. a cyclic ether such as tetrahydrofuran or an amide, e.g. a substituted amide such as dimethylformamide, in the presence of a reducing agent, for example sodium dithionite, at a temperature ranging from ambient temperature to the reflux temperature of the solvent.

The pyrimidines of general formula (X) may be prepared from the intermediate of formula (XI)

(XI)

and amines of general formula (IX), using comparable conditions to those outlined for the preparation of intermediates of general formula (VII), and conditions described in C. W. Noell et al., J. Med. Chem., 5, 558 (1962). Amines of general formula (IX) are either commercially available or are readily accessed from commercially available compounds, using methodology known to those skilled in the art. This would include, where appropriate, homochiral starting materials for the generation of single isomer compounds of formula (I). As a yet further extension of the present invention, compounds of formula (I) in which $R^1$ is H and $R^2$ is H or $NH_2$ can be prepared from intermediates of general formula (XII) via hydrolysis.

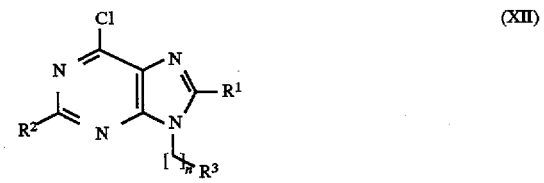
(XII)

The hydrolysis reaction may be performed using standard conditions for hydrolysis reactions of this type. Thus, for example the reaction may be carried out in a solvent, such as water, optionally in the presence of a cosolvent, for example an inert organic solvent such as an alcohol, e.g. methanol or an amide, e.g. a substituted amide sich as dimethylformamide in the presence of an inorganic hydroxide containing base, e.g. sodium hydroxide, at an elevated temperature such as the boiling point of the solvent.

Intermediates of general formula (XII) may be prepared by coupling a purine of general formula (XIII)

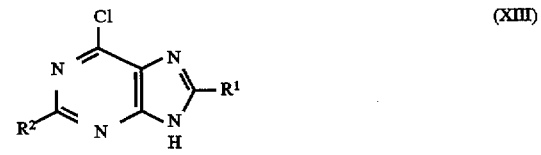
(XIII)

with an intermediate of general formula (XIV)

(XIV)

in which $R^9$ represents a halogen or a suitable leaving group such as an alkylsulphonate ester, e.g. methanesulphonate, or an arylsulphonate ester, e.g. 4-toluenesulphonate.

Intermediates of general formula (XIII) are either commercially available or may be made using methods evident to those skilled in the art.

The coupling reaction may be performed using standard conditions for reactions of this type. Thus, for example the reaction may be achieved in a solvent, for example an inert organic solvent such as an ether, e.g. a cyclic ether such as tetrahydrofuran, an amide e.g. a substituted amide such as dimethylformamide or an alcohol such as methanol, in the presence of a suitable base, for example an inorganic base such as potassium carbonate, or an organic base such as an amine, e.g. triethylamine, at a temperature between ambient temperature and the reflux temperature of the solvent, preferably 80° C.

Intermediates of general formula (XIV) are either commercially available or are readily accessed from commercially available compounds, using methodology known to those skilled in the art. This would include, where appropriate, homochiral starting materials for the generation of single isomer compounds of formula (I).

As a yet further extension of the present invention, compounds of formula (I) can be prepared from intermediates of general formula (XV) via deprotection. Where $R^{10}$ represents a group such as benzyl or substituted benzyl that can be removed using standard conditions for removal of such groups. Thus, for example the reaction may be carried out in a solvent such as an alcohol, such as ethanol, optionally in the presence of an acid, for example an inorganic acid such as hydrochloric acid. In the presence of a catalyst, for example palladium on charcoal catalyst under an atmosphere of hydrogen gas at ambient temperature.

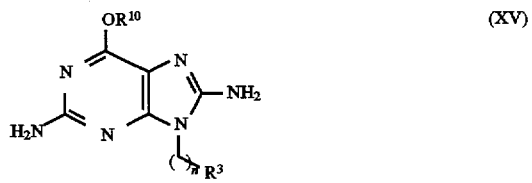

(XV)

Intermediates of the general formula (XV) may be prepared by coupling a purine of general formula (XVI)

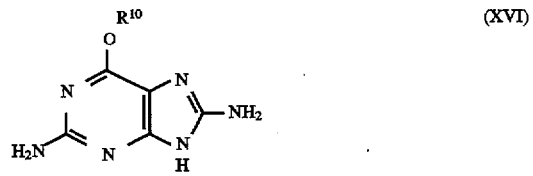

(XVI)

with an intermediate of general formula (XIV) in which $R^9$ and $R^3$ are as previously described.

The coupling reaction may be performed using standard conditions for reactions of this type. Thus, for example the reaction may be achieved in a solvent, for example an inert organic solvent such as an amide e.g. a substituted amide such as dimethylformamide in the presence of a suitable base, for example an inorganic base such as sodium hydride, at a temperature between ambient temperature and the reflux temperature of the solvent, preferably 80° C. Intermediates of general formula (XVI) may be prepared by a modification of the procedure given by S. Ram et al Heterocycles 1978, 22 (1984) or M.-Y. Chae et al J. Med. Chem. 359, 38(2), (1995).

As a further aspect of this invention an intermediate of general formula (XVI) may be used in the production of compounds of general formula (I) wherein $R^3$ is other than that previously defined, using the same methodology for the production of intermediates of general formula (XV), where $R^3$ may also represent H, $C_{1-6}$ alkyl-$R^6$, aryl, substituted aryl, heteroaryl, substituted heteroaryl, $C_{3-9}$ cycloalkyl or substituted $C_{3-9}$-cycloalkyl and $R^6$ is as previously defined. For $R^3$=aryl or heteroaryl, n=1 or 2.

Compounds of formula (I) may also be prepared by interconversion of other compounds of formula (I). Thus for example, a compound of formula (I) where $R^3$ contains a group $R^4$ where $R^4$ is $C_{1-6}$ alkyl-$R^6$ and $R^6$ is $CO_2H$, can be converted into another such compound of formula (I) where $R^6$ represents $CO_2C_{1-6}$ alkyl, using methods evident to those skilled in the art.

The invention also relates to any novel starting materials and processes for their manufacture.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds of the invention or intermediates can also be obtained in the form of their hydrates, or include other solvents used for their crystallization. This invention also relates to a method of treatment for patients (including man and/or mammalian animals raised in the dairy, meat or fur industries or as pets) suffering from disorders or diseases associated with purine nucleoside phosphorylase as outlined above, and more specifically, a method of treatment involving the administration of the purine nucleoside phosphorylase inhibitors of formula (I) as the active constituents.

Accordingly, the compounds of formula (I) can be used among other things in the treatment of autoimmune diseases, transplant rejection, psoriasis, gout, rheumatoid arthritis, myasthenia gravis, Type I diabetes, discoid lupus erythematosis, systemic lupus erythematosis, multiple sclerosis, T-cell cancers including but not limited to T-cell leukaemia and cutaneous T-cell lymphoma, atopic dermatitis, contact dermatitis or other chronic allergic conditions, eczema, irritable bowel disease or malaria. Additionally, the compounds of formula (I) can be used to potentiate the antiviral and antitumor effect of antiviral or antitumor purine nucleosides that may be metabolically degraded by PNP. Hence, a further embodiment of the invention relates to a method of inhibiting the phosphorolysis and metabolic breakdown of antiviral or antitumour purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g. of 2'-deoxyguanosine, 2'3'-dideoxyinosine, 2',3'-dideoxyguanosine or 2',3'-dideoxyadenosine.

Furthermore, the invention thus relates to a method of potentiating the antiviral or antitumor effect of a 2' or 3'-monodeoxypurine nucleosides or of 2',3'-dideoxypurine nucleosides in mammals which comprises adminstering in conjunction therewith to a mammal in need thereof, either separately on in combination with a said nucleoside, an effective purine nuceloside phosphorylase inhibiting amount of a compound of the invention preferably in combination with one or more pharmaceutically acceptable carriers.

More particuarly, such relates to a method of enhancing or potentiating the effect of 2',3'-dideoxypurine nucleosides known in the art, e.g. 2',3'-dideoxyinosine, 2',3'-dideoxyguanosine or 2',3'-dideoxyadenosine for the treatment of retrovirus infections, e.g. HIV-retrovirus infections (acquired immunodeficiency syndrome, AIDS). 2',3'-Dideoxypurine nucelosides are known in the art as inhibitors of HIV retrovirus infectivity and to be metabolically degraded by PNP, e.g. as described in Biochemical Pharmacology, 22, 3797 (1987). Such are administered at a pharmaceutically acceptable dose which is effective in inhibiting HIV-retrovirus infections. Preferably the lowest possible effective dose is used.

The invention further relates to pharmaceutical compositions suitable for enteral, such as oral or rectal, topical and parenteral administration, or by inhalation spray to mammals including man, which are useful to inhibit purine nucleoside phosphorylase activitiy and for the treatment of disorders responsive thereto, comprising an effective amount of a pharmacologically active compound of the invention, alone or in combination, with one or more pharmaceutically acceptable carriers. The term parenteral as used herein includes subcutaneous injections, intravenous, intrasternal injection or infusion techniques.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, hydroxypropylmethylcellulose, sodium alginate, polyvinylpyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agents and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acaia or gum tragacanth, naturally-occuring phosphatides, for example soya bean, lecithin, and esters or partial esters dervied from fatty acids and hexitol anhydrides, for example sorbitan monooleate and condensation products of the said partial esters with ethylene oxide, for example polyoxyethylene sorbitan monooleate. The emulsions may also contain sweetening and flavouring agents. Syrups and elixirs may be formulated with sweetening agents, for example glycerol, propylene glycol, sorbitol and sucrose. Such formations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as folic acid find use in the preparation of injectables.

The compounds of formula (I) may also be adminstered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the compounds of formula (I) are employed. (For purposes of this application, topical application shall include mouth washes and gargles.) Dosage levels of the order of from about 0.05 mg to about 2,000 mg per kilogram of body weight per day are useful in the treatment of the above-indicated conditions (about 2.5 mg to about 100 g per patient per day). For example, rheumatoid arthritis may be effectively treated by the administration of from about 0.01 to 100 mg of the compound per kilogram of body weight per day (about 0.5 mg to about 7 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples 1 to 19 illustrate the compounds of the invention and their preparation (via the given Intermediates, as appropriate).

In the Examples, the following abbreviations are used:

| | |
|---|---|
| DEAD | Diethyldiazodicarboxylate |
| DMF | Dimethylformamide |
| DCC | Dicyclohexylcarbodiimide |
| RT | Room temperature |
| THF | Tetrahydrofuran |
| MsCl | Methanesulfonyl chloride |

Intermediate 1

2-Amino-5-nitro-4-(2'-tetrahydrofuranylmethylamino)-pyrimidin-6-[1H]-one

To a stirred suspension of 2-Amino-4-chloro-5-nitropyrimidin-6-[1H]-one (C. Temple et al., Nucleic Acid Chemistry, Vol. I (1978), Wiley N.Y., P47–52) (2 g) in ethanol (45 ml) was added triethylamine (1.1 g) and tetrahydrofurylamine (1.1 g) and this was heated at reflux for 1.5 h. The reaction mixture was cooled to RT and filtered. The residue was washed with water (2×20 ml) and ethanol (5 ml) and the solid dried in vacuo overnight to give a pale yellow solid (2.5 g).

TLC Rf=0.10 (20% MeOH/CH$_2$Cl$_2$)

Intermediate 2

2-Amino-4-(2'-tetrahydrofuranylmethylamino)-5-[1-[3-(ethoxycarbonyl)thioureido]]pyrimidin-6-[1H]-one Intermediate 1 (1.0 g) was suspended in water at 65°–80° C. and sodium dithionite (4.5 g) added in small portions. After 0.5 h the precipiated solid was filtered and resuspended in acetonitrile (40 ml). Ethoxycarbonylisothiocyanate (1.5 g) was then added and the reaction mixture heated at reflux for 3 h. After ice cooling the suspended solid was filtered and washed with acetonitrile (10 ml) and dried in vacuo to give the title compound (0.5 g).

TLC Rf=0.3 (10% MeOH/CH$_2$Cl$_2$)

Intermediate 3

Ethyl 6-amino-4-(2'-tetrahydrofuranylmethylamino) oxazolo-[5,4-d]-pyrimidine-2-carbamate Intermediate 2 (0.42 g) was dissolved in DMF (20 ml) and DCC (0.73 g) added in one portion. After 48 h at RT the solvent was removed in vacuo. The residue was treated with hot toluene and the solid filtered and washed with hot toluene. The residue was dried in vacuo to give the title compound (0.31 g).

TLC Rf=0.45 (10% MeOH/CH$_2$Cl$_2$)

Intermediate 4

2-Amino-5-nitro-4-(2'-tetrahydropyranylmethylamino)pyrimidin-6-[1H]-one

The title compound was made from 2-aminomethyltetrahydropyran (GB 1031916) in a similar manner to Intermediate 1.

TLC Rf=0.6 (10% MeOH/CH$_2$Cl$_2$)

Intermediate 5

2-Amino-4-(2'-tetrahydropyranylmethylamino)-5-[1-[3-(ethoxycarbonyl)thioureido]]pyrimidin-6-[1H]-one The title compound was made from Intermediate 4 in a similar manner to Intermediate 2.

TLC Rf=0.3 (10% MeOH/CH$_2$Cl$_2$)

Intermediate 6

Ethyl 6-amino-4-(2'-tetrahydropyranylmethylamino) oxazolo-[5,4-d]-pyrimidine-2-carbamate The title compound was made from Intermediate 5 in a similar manner to Intermediate 3.

TLC Rf=0.5 (10% MeOH/CH$_2$Cl$_2$)

Intermediate 7

(R)-2-Hydroxymethyltetrahydropyran

To a stirred solution of (R) 2-hydroxymethyl-2,3-dihydropyran (S.-Kang et al, Tet. Asym. 1995, 6(i), 97–100) (0.23 g) in ethanol (40 ml) was added Palladium on carbon catalyst (10% Pd). The whole was placed in a Parr reaction vessel and stirred under 100 psi hydrogen for 5 h, after which time the solution was filtered and concentrated in vacuo to give the title compound (0.2 g) as a yellow oil. $^1$H NMR (400 MHz, DMSOd$_6$): 1.0(M, 1H), 1.5(m,5H), 1.8(bs, 1H), 3.3 (m,3H), 3.8(d,1H), 4.5(bs, 1H)

Intermediate 8

(R)-2-Methylsulphonyloxymethyltetrahydropryran

Intermediate 7 (0.85 g), CH$_2$Cl$_2$ (27 ml) and triethylamine (2 ml) were combined and cooled to 0° C. (ice bath) under N$_2$. To this was added MsCl (0.62 ml) dropwise via syringe and stirring continued as the reaction warmed to RT. Stirring was continued for a further 5 h, after which time the product was concentrated onto silica and purified by flash chromatography to give the title compound (1.31 g) as a yellow oil.

TLC Rf=0.6 (50% EtOAc/hexane)

Intermediate 9

(R)-2,8-Diamino-6-benzyloxy-9-[2 (tetrahydropyranylmethyl)]purine

To a stirred solution of 2,8-diamino-6-benzyloxypurine (Chae et al J.Med. Chem 1995, 38(2), 359–365) (0.23 g) in DMF (2 ml) was added LiH (8.2 mg) and the mixture stirred for 45 minutes under $N_2$. Intermediate 8 (0.17 g) was then added as a solution in DMF (1.5 ml) and the whole gradually heated to 80° C. and maintained at that temperature for 20 h. The product was then concentrated onto silica and purified by flash chromatography to give the title compound (43.7 mg) as a buff coloured solid.

TLC Rf=0.8 (10%MeOH/$CH_2Cl_2$

Intermediate 10

(S)-2-Hydroxymethyltetrahydropyran

Intermediate 10 was prepared in the same manner as Intermediate 7, to give a pale yellow oil.

$^1$H NMR (400 MHz, $CDCl_3$) 1.3(m,1H), 1.5(m,4H), 1.8(m,1H), 2.3(bs,1H), 3.5(m,4H) 4.0(m, 1H)

Intermediate 11

(S)-2-Methylsulphonyloxymethyltetrahydropyran

Intermediate 11 was prepared in the same manner as Intermediate 8, to give a pale yellow, viscous oil.

TLC Rf=0.49 (50%EtOAc/hexane)

Intermediate 12

(S)-2,8-Diamino-6-benzyloxy-9-[2'-(tetrahydropymnylmethyl)]purine

The title compound was made from Intermediate 11 in a similar manner to Intermediate 9.

TLC Rf=0.8 (10% MeOH/$CH_2Cl_2$)

Intermediate 13

2-Methylsulphonyloxymethyl-6-methyltetrahydropyran

Intermediate 13 was made from 2-hydroxymethyl-6-methyltetrahydropyran (E. I. Klimova et al Zh. Org. Khim, 1970, 6, 413–418) in a similar manner to Intermediate 8.

TLC Rf=0.26 (50% EtOAc/hexane)

Intermediate 14

2,8-Diamino-6-benzyloxyl-9-[2'-(6'-methyltetrahydropyranyl)methyl]purine

The title compound was made from Intermediate 13 in a similar manner to Intermediate 9.

TLC Rf=0.82 (10% MeOH/$CH_2Cl_2$)

Intermediate 15

2-Methylsulphonyloxymethyl-4-methyltetrahydropyran

Intermediate 15 was prepared in the same manner as Intermediate 8, thus 2-hydroxymethyl-4-methyl tetrahydropyran (B. L. Eliel et al, Org. Mag. Res. 1983, 21, 95–107) (0.35 g) gave 0.43 g of Intermediate 15 as a yellow oil.

TLC Rf=0.64 (50%EtOAc/hexane)

Intermediate 16

2,8-Diamino-6-benzyloxy-9-[2'-(4'-methyltetrahydropyranyl)methyl)purine

The title compound was made from Intermediate 15 in a similar manner to Intermediate 9.

TLC Rf=0.87 (10% MeOH/$CH_2Cl_2$)

Intermediate 17

2-Methylsulphonyloxymethyl-trans-4,6-dimethyltetrahydropyran

Intermediate 17 was made from 4,6-dimethyl-2-hydroxymethyltetrahydropyran (B. L. Eliel et al Org. Mag. Res. 1983, 21, 95–107) in a similar manner to Intermediate 8.

TLC Rf=0.83 (50% EtOAc/hexane)

Intermediate 18

2,8-Diamino-6-benzyloxy-9-[2'(4',6'-dimethyltetrahydropyranyl)methyl)]purine

Intermediate 18 was made from Intermediate 17 in a similar manner to Intermediate 9.

TLC Rf=0.85 (10% MeOH/$CH_2Cl_2$)

Intermediate 19 tert-Butyl-6-(acetoxymethyl) tetrahydro-2H-pyran-2-acetate

Aluminium trichloride (1 g) was cooled to −78° C. under a nitrogen atmosphere and dichloromethane (15 ml) was added. A solution of trans-6-(benzenesulfonyl)tetrahydro-2H-pyran-2-methanol acetate (1 g) (S. V. Ley et al, Tetrahedron (1989), 45 (13), 4293) and 1-tert-butyloxy-1-trimethylsilyloxyethene (1.37 g) in dichloromethane (10 ml) was then added dropwise. The reaction was stirred at −78° C. for 2.5 h, then room temperature for 1.5 h. After quenching with 1N HCl and extracting with dichoromethane the crude product was purified by flash chromatography (50% EtOAc/hexane) to give the title compound (187 mg).

TLC Rf=0.6 (50% EtOAc/hexane)

Intermediate 20 tert-Butyl-6-(hydroxymethyl)tetrahydro-2H-pyran-2-acetate

Intermediate 19 (0.19 g), potassium carbonate (0.19 g) and methanol (3.5 ml) were combined and stirred at room temperature 2.5 h. Dilution with water and extraction with ethyl acetate gave the title compound (0.11 g).

TLC Rf=0.33 (50% EtOAc/hexane)

Intermediate 21 tert-Butyl-6-(methylsulfonyloxymethyl)tetrahydro-2H-pyran-2-acetate

The title compound was made from Intermediate 20 in a similar manner to Intermediate 8.

TLC Rf=0.4 (50% EtOAc/hexane)

Intermediate 22

2,8-Diamino-6-benzyloxy-9-(2'-(6'-tert-butyloxycarboxymethyl) tetrahydro-[2H]-pyranmethyl)purine The title compound was made from Intermediate 21 in a similar manner to Intermediate 9.

TLC Rf=0.3 (EtOAc)

Intermediate 23 trans-Tetrahydro-2-acetoxymethyl-6-prop-2-enyl-[2H]-pyran

Aluminium trichloride (1 g) was cooled to −78° C. under a nitrogen atmosphere and dichloromethane (15 ml) was added. A solution of trans-6-(benzenesulfonyl)tetrahydro-2H-pyran-2-methanol acetate (S. V. Ley et al., Tetrahedron (1989), 45 (13), 4293) (1 g) and allyl trimethylsilane (835 mg) in dichloromethane (10 ml) was then added dropwise. The reaction was stirred at −78° C. for 2 h, then −35° C. for 1 h. After quenching with 1N HCl and extracting with dichloromethane the crude product was purified by flash chromatography (40% EtOAc/hexane) to give the title compound of (414 mg).

TLC Rf=0.6 (50% EtOAc/hexane)

Intermediate 24 trans-Tetrahydro-2-hydroxymethyl-6-prop-2-enyl-2H-pyran

The title compound was made from Intermediate 23 in a similar manner to intermediate 20.

TLC Rf=0.37 (50% EtOAc/hexane)

Intermediate 25 trans-Tetrahydro-2-methylsulfonyloxymethyl-6-prop-2-enyl-2H-pyran

The title compound was made from Intermediate 24 in a similar manner to intermediate 21.

TLC Rf=0.45 (50% EtOAc/hexane)

Intermediate 26

(S*, S*)-2, 8-Diamino-(>-benzyloxy-9-(2'-(6'-propyl)-tetrahydro-2H-pyranylmethyl) purine The title compound was made from Intermediate 25 in a similar manner to Intermediate 9.

TLC Rf=0.55 (10% MeOH/CH$_2$Cl$_2$)

Intermediate 27 trans-Tetrahydro-2-ten-butyldimethylsiloxymethyl-6-prop-2-enyl-2H-pyran

Intermediate 24 (3.75 g), DMF (20 ml), imidazole (3.6 g) and tert-butyldimethylsilylchloride (4 g) were combined and stirred at room temperature 18 h. Dilution with water, extraction with dichloromethane and purification of the crude product by flash chromatography (50% EtOAc/hexane) gave the title compound (5.18 g).

TLC Rf=0.65 (50% EtOAc/hexane)

Intermediate 28 trans-2-tert-Butyldimethylsiloxymethyl-6-hydroxypropyl tetrahydro-2H-pyran

Intermediate 27 (2.7 g) and tetrahydrofuran (10 ml) were combined under an atmosphere of nitrogen and cooled in a ice bath. BH$_3$. THF (1M soln. in THF) (5 ml) was added dropwise and the reaction was stirred at room temperature 18 h. The reaction was cooled to 0° C. again and 1N NaOH (30 ml) and hydrogen peroxide (27% w/w) (10 ml) were added. The reaction was stirred at room temperature for 3.5 h. Extraction with ethyl acetate and purification of the crude product by flash chromatography (30% EtOAc/hexane) gave the title compound (0.54 g).

TLC Rf=0.3 (50% EtOAc/hexane)

Intermediate 29 trans-6-Benzyloxypropyl-2-tert-butyldimethylsiloxymethyltetrahydro-2H-pyran

To a stirred suspension of sodium hydride (60% dispersion in mineral oil) (90 mg) in anhydrous tetrahydrofuran (5 ml) was added Intermediate 28 (0.54 g) at RT under nitrogen. The mixture was warmed to 30° C., left to stir for 15 minutes and cooled back to RT. Benzyl bromide (0.27 ml) was added and the reaction mixture was left to stir at RT for 4.5 h. The reaction mixture was evaporated in vacuo onto silica and purified by flash chromatography (SiO$_2$, 50%EtOAc/hexane) to give a clear colourless liquid (1.1 g).

TLC Rf=0.6 (50%EtOAc/hexane)

Intermediate 30 trans-6-Benzyloxypropyl-2-hydroxymethyltetrahydro-[2H]-pyran

Intermediate 29 (0.6 g) in a 1M solution of tetrabutylammonium flouride in THF (3.5 ml) was stirred at RT for 16 h. The reaction mixture was evaporated down in vacuo onto silica and purified by flash chromatography (SiO$_2$, 50%EtOAc/hexane) to give a clear colourless liquid (0.28 g).

TLC Rf=0.2 (50%EtOAc/hexane)

Intermediate 31 trans-6-Benzyloxypropyl-2-methylsulphonyloxymethyltetrahydro-[2H]-pyran

The title compound was made from Intermediate 30 in a similar manner to Intermediate 8.

TLC Rf=0.3 (50%EtOAc/hexane)

Intermediate 32

6-Benzyloxy-9[trans-2'-(6'-benzyloxypropyl) tetrahydro-[2H]-pyranylmethyl]-2,8-diaminopurine Intermediate 32 was made from Intermediate 31 in a similar manner to Intermediate 9.

TLC Rf=0.7 (10% MeOH/CH$_2$Cl$_2$)

Intermediate 33 trans-2-tert-Butyldimethylsiloxymethyl-6-methoxycarbonylethyltetrahydro-[2H]-pyran Acetonitrile (4 ml) carbontetrachloride (4 ml) and water (6 ml) were added to intermediate 28 (0.98 g) and sodium periodate (2.18 g). Ruthenium (III) chloride hydrate (5 mg) was added and the mixture was vigorously stirred at RT for 2.5 h. The reaction mixture was diluted with 1M HCl and extracted with CH$_2$Cl$_2$. The organic extracts were combined, dried (MgSO$_4$) and the solvent removed in vacuo to give a gum, which was taken up in diethyl ether. The solution was cooled to 0° C. and treated with diazomethane (H. J. Backer et al., Organic Synthesis, Col. Vol. V, 351) (8.3 mmol). The reaction was stirred at RT for 22 hours. The solvent was removed in vacuo and the residue was purified by flash chromatography (SiO$_2$, 50%EtOAc/hexane) to give a clear colourless liquid (0.50 g).

TLC Rf=0.6 (50% EtOAc/hexane)

Intermediate 34 trans-2-Hydroxymethyl-6-methoxycarbonylethyltetrahydro-2H-pyran

The title compound was made from Intermediate 33 in a similar manner to Intermediate 30.

TLC Rf=0.1 (1:1 EtOAc/hexane)

Intermediate 35 trans-6-Methoxycarbonylethyl-2-methylsulphonyloxymethyltetrahydro-2H-pyran

The title compound was made from Intermediate 34 in a similar manner to Intermediate 8.

TLC Rf=0.7 (EtOAc)

Intermediate 36

6-Benzyloxy-2,8-diamino-9-(trans-2'-(6'-methoxycarbonylethyl) tetrahydro-[2H]-pyranylmethyl) purine The title compound was made from Intermediate 35 in a similar manner to Intermediate 9.

TLC Rf=0.7 (10% MeOH/CH$_2$Cl$_2$)

Intermediate 37

(±) Methylsulphonyloxymethyl-1,4-dioxan

The title compound was made from (+) Hydroxymethyl-1,4-dioxan (R. I. Duclos et al., Journal of Organic Chemistry 1992, 57, 6156–6163) in a similar manner to Intermediate 8.

TLC Rf=0.4 (50%EtOAc/hexane)

Intermediate 38

6-Benzyloxy-2,8-diamino-9-[2'-(1',4'-dioxanyl) methyl]purine

The title compound was made from Intermediate 37 in a similar manner to Intermediate 9.

TLC Rf=0.7 (10% MeOH/CH$_2$Cl$_2$)

Intermediate 39

2-Hydroxymethyltetrahydrothiophene

Calcium chloride (10 g) was added to a solution of methyl tetrahydrothiophene-2-carboxylate (J. Wrobel and E. Hejchman, Bull. Polish Acad. Sci. Chem. 1987, 3521) (10.0 g) in ethanol (200 ml) and the mixture stirred for 30 min. Sodium borohydride (5.2 g) was added and the suspension stirred overnight, then poured into iced 1M HCl (500 ml) and extracted with CH$_2$C$_1$. The combined extracts were washed with water and brine, dried and evaporated in vacuo to give the title compound as colourless liquid (7.05 g).

TLC Rf=0.22 (20% EtOAc/CH$_2$Cl$_2$)

Intermediate 40

2-phthalimidomethyltetrahydrothiophene

A solution of DEAD (11 g) in dry THF (20 ml) was added to a solution of Intermediate 39 (7.3 g), phthalimide (10.2 g) and triphenylphosphine (17 g) in dry THF and the solution was stirred overnight, then evaporated and the residue triturated with ether. The solid residue was filtered off and the filtrate evaporated and purified by flash chromatography (15% EtOAc/hexanes) to give the title compound as a white solid (10.5 g).

TLC Rf=0.38 (20% EtOAc/hexanes)

Intermediate 41

2-Aminomethyltetrahydrothiophene

Hydrazine hydrate (2.52 g) was added to a solution of Intermediate 40 in EtOH (60 ml) and the mixture was boiled under reflux for 3 h, then cooled and filtered and the filtrate evaporated. The residue was chromatographed (5% MeOH/CH$_2$Cl$_2$) to give the title compound as pale yellow liquid (3.25 g).

TLC Rf=0.41 (5% MeOH/CH$_2$Cl$_2$)

Intermediate 42

2-Amino-5-nitro4-(2'-tetrahydrothienylmethylamino)-pyrimidine-6-[1H]-one

The title compound was made from Intermediate 41 in a similar manner to Intermediate 1.

TLC Rf=0.15 (20% MeOH/CH$_2$Cl$_2$)

Intermediate 43

2-Amino4-(2'-tetrahydrothienylmethylamino)-5-[1-[3-(ethoxycarbonyl)thioureido]]pyrimidin-6-[1H]-one The title compound was made from Intermediate 42 in a similar manner to Intermediate 2.

TLC Rf=0.32 (10% MeOH/CH$_2$Cl$_2$)

Intermediate 44

Ethyl 6-amino4-(2'-tetrahydrothienylmethylamino) oxazolo[5,4-d]pyrimidine-2-carboxylate The title compound was made from Intermediate 43 in a similar manner to Intermediate 3.

TLC Rf=0.53 (10% MeOH/CH$_2$Cl$_2$)

Intermediate 45

2-Amino-5-nitro4-(2'-(1-tert-butoxycarbonyl) pyrrolidinylmethylamino-5-nitropyrimidin-6-[1H]-one The title compound was made from 1-tert-butoxycarbonyl-2-aminomethylpyrrolidine in a similar manner to Intermediate 1.

TLC Rf=0.14 (20% MeOH/CH$_2$Cl$_2$)

Intermediate 46

2-Amino4-(2'-(tert-butoxycaxbonylpyrrolidinylmethyl)amino)-5-[1-[3-ethoxycarbonylthioureido]]pyrimidin-6-one The title compound was made from Intermediate 45 in a similar manner to Intermediate 2.

TLC Rf=0.23 (10% MeOH/CH$_2$Cl$_2$)

Intermediate 47

Ethyl 6-amino4-(2'-(1'-tert-butoxycarbonylpyrrolidinylmethyl) amino)oxazolo [5,4-d]pyrimidine-2-carbamate The title compound was made from Intermediate 46 in a similar manner to Intermediate 3.

TLC Rf=0.42 (10% MeOH/CH$_2$Cl$_2$)

Intermediate 48

8-Amino-9-(2'-(1'-tert-butorycarbonylpyrrolidinyl)) guanine

The title compound was made from Intermediate 47 in a similar manner to Example 1.

TLC Rf=0.45 (25% MeOH/CH$_2$Cl$_2$)

Intermediate 49

5-(tert-Butyldimethylsilyloxymethyl)pyrrolidin-2-one

The title compound was made from 5-hydroxymethylpyrrolidin-2-one in a similar manner to Intermediate 27.

TLC Rf=0.4 (5% MeOH/CH$_2$CH$_2$)

Intermediate 50

1-tert-Butoxycarbonylmethyl-5-tert-butyldimethylsilyloxylmethyl pyrrolidin-2-one A solution of intermediate 49 (1.0 g) in tetrahydrofuran (5 ml) was added to a suspension of sodium hydride (0.21 g) in tetrahydrofuran (20 ml) and stirred for 0.5 hours, tert-butyl bromoacetate (0.94 g) in THF (5 ml) was added. After 1.5 hours, the mixture was diluted with water and extracted with dichloromethane, washed with water and dried (MgSO$_4$). Concentration gave a colourless oil which was further purified by chromatograhph on silica. The title compound was obtained as a colourless oil (1.5 g).

TLC Rf=0.65 (5% MeOH/CH$_2$Cl$_2$)

Intermediate 51

1-tert-Butoxycarbonylmethyl-5-hydroxymethylpyrrolidin-2-one

The title compound was made from Intermediate 50 in a similar manner to Intermediate 30.

TLC Rf=0.3 (5% MeOH/CH$_2$Cl$_2$)

Intermediate 52

1-tert-Butoxycarbonylmethyl-5-methanesulphonyloxymethylpyrrolidin-2-one

The title compound was made from Intermediate 51 in a similar manner to Intermediate 8.

TLC Rf=0.45 (5% MeOH/CH$_2$Cl$_2$)

Intermediate 53

1-tert-Butoxycarbonylmethyl-5-azidomethylpyrrolidin-2-one

Sodium azide (0.55 g) was added to a solution of intermediate (52) (1.3 g) in DMF (15 ml) and heat to 50° C. for 48 hours. The reaction mixture was diluted with water (50 ml) and extracted with ether (3×100 ml). Combined ether washings were washed with water (4×50 ml), dried (MgSO$_4$) and concentrated to dryness to yield the title compound as a pale yellow oil (0.7 g).

TLC Rf=0.6 (5% MeOH/CH$_2$Cl$_2$)

Intermediate 54

1-tert-Butoxycarbonylmethyl-5-aminomethylpyrrolidin-2-one

Intermediate 53 (4.8 g) and triphenylphosphine (10.5 g) were dissolved in THF (100 ml) and water (5 ml). After stirring for 48 hours the reaction mixture was evaporated to dryness and purified by chromatography on silica (5%MeOH/CH$_2$Cl$_2$). The title compound was obtained as a yellow oil (2.7 g).

TLC Rf=0.4 (5% MeOH/CH$_2$Cl$_2$)

Intermediate 55

2-Amino-4-(1'-(tert-butoxycarbonylmethyl)pyrrolidin-2-onylmethylamino)-5-nitropyrimidin-6-[1H]-one The title compound was made from Intermediate 54 in a similar manner to Intermediate 1.

TLC Rf=0.6 (10% MeOH/CH$_2$Cl$_2$)

Intermediate 56

2-Amino-4-(1'-tert-butoxycarbonylmethylpyrrolidin-2'-onyl-5'-methylamino)-5-[1-[3-(ethoxycarbonyl)thioureido]]pyrimidin-6-[1H]-one The title compound was made from Intermediate 55 in a similar manner to Intermediate 2.

TLC Rf=0.45 (10% MeOH/CH$_2$Cl$_2$)

Intermediate 57

Ethyl 6-amino-4-(1'-tert-butoxycarbonylmethylpyrrolidin-2'-onyl-5'-methylamino)-oxazolo[5,4,d]pyrimidine-2-carbamate The title compound was made from Intermediate 56 in a similar manner to Intermediate 3.

TLC Rf=0.55 (10% MeOH/CH$_2$Cl$_2$)

Intermediate 58

9-(1'-Carboxymethylpyrrolidin-2'-one-5'-ylmethyl)-8-ethoxycarbonylaminoguanine

To a solution of intermediate 57 (0.85 g) in water (30 ml) was added potassium carbonate (0.14 g) and refluxed for 24 hours. The resultant mixture was then stirred at ambient temperature for 1 week and the precipitate recovered by filtration. The filtrate was evaporated to dryness to give the title compound (0.36 g).

[M+H]$^+$=394

EXAMPLE 1

8-Amino-9-(2'-tetrahydrofuranylmethyl)guanine

Intermediate 3 (0.27 g) was heated at reflux with potassium carbonate (0.23 g) in methanol (25 ml) for 6 h. The methanol was removed in vacuo and replaced with water (25 ml) and heated at reflux for 6 h. The cooled reaction mixture was neutralised with saturated ammonium chloride solution. The resultant solid was dissolved in aqueous sodium hydroxide solution and precipitated by addition of acetic acid. The precipitate was filtered, washed (water) and dried to give the title compound (0.23 g).

TLC Rf=0.2 (30% MeOH/CH$_2$Cl$_2$)

$^1$H NMR (200 MHz; DMSO-d$_6$), 1.6–2.1 (m,4H), 3.7 (m, 1H), 3.95 (m,3H), 4.25 (m, 1H), 5.5 (bs,2H), 6.1 (bs,2H), 10.3 (bs, 1H).

EXAMPLE 2

8-Amino-9-(2'-tetrahydropyranylmethyl)guanine

The title compound was made from Intermediate 6 in a similar manner to Example 1.

TLC Rf=0.1 (10% MeOH/CH$_2$Cl$_2$)

$^1$H NMR (200 MHz; DMSO-d$_6$), δ1.0–1.9 (m,6H), 3.3 (m,1H), 3.6 (m,1H), 3.8 (m,3H), 5.8 (bs,2H), 6.3 (bs,2H), 10.6 (bs,1H)

EXAMPLE 3

8-Amino-9-(2'-tetrahydropyranylmethyl)guanine hydrochloride

Acetyl chloride (14 ml) was added to methanol at 0° C. and the solution was stirred for 10 minutes. Example 2 was added to the solution and the mixture was stirred at RT for 1 h. The solvent was removed in vacuo to give a white solid which was dried at 80° C. in a vacuum oven (0.64 g). HPLC (Novapak C-18 100×8mm, 2:3 MeOH/H$_2$O, 1 ml/min). R$_t$ 8.75 minutes.

$^1$H NMR (200MH$_2$; DMSO-d$_6$), 1.1–1.9 (m, 6H), 3.3 (m, 1H), 3.7 (m, 1H), 3.8–4.2 (m, 3H), 7.1 (bs, 2H), 8.2 (s, 2H), 11.4 (s, 1H).

EXAMPLE 4

(R) 8-Amino-9-[2'(tetrahydropyranylmethyl)] guanine dihydrochloride

Intermediate 12 (38 mg) was stirred in a stream of N$_2$ with HCl (1 ml) in ethanol (9 ml). Pd/carbon catalyst (10% d) (5 mg) was then added and the whole stirred under an atmosphere of hydrogen for 3 hours. The reaction was filtered and the solvent removed in vacuo to give the title compound as a white solid (22.6 mg).

TLC Rf=0.43 (20% MeOH/CH$_2$Cl$_2$)

[M+H]$^+$=338

EXAMPLE 5

(S) 8-Amino-9-(2'-tetrahydropyranylmethyl)guanine dihydrochloride

The title compound was made from Intermediate 9 in a similar manner to Example 4.

TLC Rf=0.25 (20% MeOH/CH$_2$Cl$_2$)

[M+H]$^+$=338

EXAMPLE 6

8-Amino-9-[2'-(6'-methyltetrahydropyranyl)methyl] guanine dihydrochloride

The title compound was made from Intermediate 14 in a similar manner to Example 4.

TLC Rf=0.05 (10% MeOH/CH$_2$Cl$_2$)

[M+H]$^+$=279

EXAMPLE 7

8-Amino-9-[2'-(4'-methyltetrahydropyranyl)methyl)] guanine dihydrochloride

The title compound was made from Intermediate 16 in a similar manner to Example 4.

TLC Rf=0.1 (10% MeOH/CH$_2$Cl$_2$)

[M+H]$^+$=279

EXAMPLE 8

8-Amino-9-[2'(4',6'-dimethyltetrahydropyranylmethyl)]guanine dihydrochloride

The title compound was made from Intermediate 18 in a similar manner to Example 4.

TLC Rf=0.15 (10% MeOH/CH$_2$Cl$_2$)

[M+H]$^+$=293

EXAMPLE 9

8-Amino-9-(2'-(6'-carboxymethyl) tetrahydropyranylmethyl)guanine dihydrochloride The title compound was made from Intermediate 22 in a similar manner to Example 4.

TLC Rf=0.1 (10% MeOH CH$_2$Cl$_2$)

[M+H]$^+$=323

EXAMPLE 10

(S*,R*)-8Amino-9-(2'-(6'-propyl)tetrahydro-2H-pyranylmethyl)guanine dihydrochloride The title compound was made from Intermediate 26 in a similar manner to Example 4.

TLC Rf=0.1 (10% MeOH/CH$_2$Cl$_2$)

[M+H]$^+$=307

EXAMPLE 11 trans-8-Amino-9-(2'-(6'-hydroxypropyl)tetrahydro-2H-pyranylmethyl)guanine dihydrochloride The title compound was made from Intermediate 32 in a similar manner to Example 4.

TLC Rf=0.05 (10% MeOH/CH$_2$Cl$_2$)

[M+H]$^+$=323

EXAMPLE 12 trans-8-Amino-9-(2'-(6'-methoxycarbonylethyl) tetrahydropyranylmethyl)guanine dihydrochloride The title compound was made from Intermediate 36 in a similar manner to Example 4.

TLC Rf=0.1 (10% MeOH/CH$_2$Cl$_2$).

[M+H]$^+$=351

EXAMPLE 13

8-Amino-9-(2'-[1,4-dioxanyl]methyl) guaninedihydrochloride

The title compound was made from Intermediate 38 in a similar manner to Example 4.

TLC Rf=0.12 (10%MeOH/CH$_2$Cl$_2$)

[M+H]$^+$=267

EXAMPLE 14

8-Amino-9-(2'-tetrahydrothienyl)guanine

The title compound was made from Intermediate 46 in a similar manner to Example 1.

TLC Rf=0.26 (25% MeOH/CH$_2$Cl$_2$)

$^1$H NMR (DMSO) 1.65 (2 H, m), 1.92–2.20 (2 H, m), 2.62–2.90 (2H, m), 3.70–3.97 (3 H, m), 6.00 (2 H, br s), 6.38 (2 H, br s), 10.81 (1 H, br s)

EXAMPLE 15

8-Amino-9-(2'-(1'-oxotetrahydrothienylmethyl) guanine

Hydrogen peroxide (18 ml) was added to a solution of Example 14 (41 mg) in acetic acid (3 ml) and the solution stirred for 3 h, then evaporated and the residue dissolved in sodium hydroxide solution. Saturated aqueous ammonium chloride was added and the title compound was collected by filtration and washed with water. Yield 17.5 mg.

TLC Rf=0.20 (20% MeOH/CH$_2$Cl$_2$)
[M+H]$^+$=283

EXAMPLE 16

8-Amino-9-(2'-(1',1'-dioxotetrahydrothienylmethyl)) guanine

Hydrogen peroxide (100 ml) was added to a solution of Example 14 (67 mg) in acetic acid (3 ml) and the solution stirred for 18 h, then evaporated and the residue stirred in aqueous potassium carbonate solution. The precipitated solid was collected by filtration and washed with water to give the title compound as a beige solid (40 mg).

TLC Rf=0.32 (20% MeOH/CH$_2$Cl$_2$)
[M+H]$^+$=299

EXAMPLE 17

8-Amino-9-(2'-pyrrolidinylmethyl)guanine trihydrochloride dihydrate

Intermediate 48 (56 mg) methanol (4.5 ml) and 3N hydrochloric acid (4.5 ml) were combined and stirred at room temperature for 1 h. The mixture was then evaporate in vacuo to give the title compound (35 mg)

TLC Rf=0.2 (20% MeOH/CH$_2$Cl$_2$) [M+H]$^+$=250

EXAMPLE 18

8-Amino-9-(2'-pyrrolidinylmethyl)guanine

The title compound was made from Example 17 in a similar manner to Example 1.

$^1$H NMR (200 MHz, DMSO-d$_6$), 1.4–2.0 (m, 4H), 2.8–3.0 (m, 2H), 3.2–4.0 (m. 4H), 6.1–6.5 (m, 4H), 9.7 (brs, 1H)
[M+H]$^+$=250

EXAMPLE 19

8-Amino-9-(1'-carboxymethylpyrrolidin-2'-on-5'-ylmethyl)guanine dihydrochloride

Intermediate 58 (0.1 g) was dissolved in 2M hydrochloric acid (10 ml) and heat at reflux for 48 hours. Evaporation to dryness yielded the title compound as a white solid (0.10 g).

$^1$H NMR (200 MH$_2$, DMSO-d$_6$) 1.8 (m,1H), 2.0 (m,1H), 202 (m, 1H), 2.4 (m, 1H), 4.0 (m,5H), 7.5 (bs,2H), 8.5 (s,2H), 11.5 (s, 1H).
[M+H]$^+$=322

We claim:
1. A compound of formula (I)

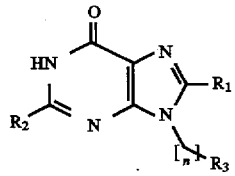

wherein:

n=0–2
R$^1$ is NH$_2$ or halogen;
R$^2$ is H or NH$_2$;
R$^3$ is any of the four groups

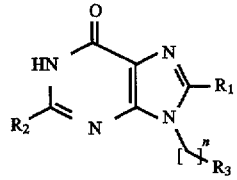

where
m=0 or 1;
X is O, NR$^5$ or S(O)$_{0-2}$ and, in group (b), the X's may be the same or different;
R$^4$ is H or one or more groups independently selected from C$_{1-6}$ alkyl-R$^6$ and aryl-R$^6$;
R$^5$ is H, C$_{1-6}$ alkyl-R$^6$, C$_{2-6}$ alkenyl, aryl, -aryl-C$_{1-6}$ alkyl, —C$_{1-6}$ alkyl-aryl, —C$_{1-6}$ alkyl-hetero(C$_{1-6}$)alkyl, CO$_2$—C$_{1-6}$ alkyl-R$^6$, CONH—C$_{1-6}$ alkyl-R$^6$, CO—C$_{1-6}$ alkyl-R$^6$ or SO$_2$—C$_{1-6}$ alkyl-R$^6$;
R$^6$ is H, CO$_2$H, CO$_2$—C$_{1-6}$ alkyl, CONH$_2$, CON(C$_{1-6}$ alkyl)$_2$, CONH(C$_{1-6}$ alkyl), CO—C$_{1-6}$ alkyl, CO-aryl, CO-heteroaryl, tetrazolyl, NHSO$_2$CF$_3$, SO$_2$NH—C$_{1-6}$ alkyl, SO$_2$N(C$_{1-6}$ alkyl)$_2$, SO$_2$NH-aryl, NHCO—C$_{1-6}$ alkyl, NHCONH—C$_{1-6}$ alkyl, NHCONH-aryl, NHSO$_2$—C$_{1-6}$ alkyl, NHSO$_2$-aryl, CN, NH$_2$, OH, O—C$_{1-6}$ alkyl or O-aryl;
in any tautomeric, salt, solvate and/or hydrate form.

2. A compound of claim 1, wherein n=1.
3. A compound of claim 1, wherein R$^1$ is NH$_2$.
4. A compound of claim 1, wherein R$^2$ is NH$_2$.
5. A compound of claim 1, wherein R$^3$ is group (a), (b), or (c), and X is O, S, or NR$^5$.
6. A compound of claim 1, wherein R$^4$ is H or C$_{1-6}$ alkyl-R$^6$.
7. A compound of claim 1, wherein R$^5$ is C$_{1-6}$ alkyl-R$^6$.
8. A compound of claim 1, wherein R$^6$ is not SO$_2$N(C$_{1-6}$ alkyl)$_2$ or CN.
9. A compound of claim 8, wherein R$^6$ is H, CO$_2$H, CO$_2$—C$_{1-6}$ alkyl, OH, NH$_2$, tetrazolyl or NHSO$_2$CF$_3$.
10. A compound of claim 8, wherein R$^3$ is group (a) or (c) where m=0.
11. A compound of claim 8, wherein R$^3$ is group (a) or (c) where m=1.
12. A compound of claim 8, wherein R$^3$ is group (b) or (d).
13. A compound of claim 1, which is 8-amino-9-(2'-tetrahydropyranylmethyl)guanine or 8-amino-9-(2'-tetrahydrofuranylmethyl)guanine.
14. A compound of claim 1, in the form of a single enantiomer.
15. A pharmaceutical composition for use in therapy, comprising a compound of claim 1 and a pharmaceutically-acceptable diluent or carrier.
16. A method for treating or preventing tissue rejection after organ or bone marrow transplantation in a human or animal, said method comprising administering an effective amount of a compound of claim 1, or a pharmaceutically-acceptable composition thereof, to said human or animal.
17. A method for the selective suppression of mammalian T-cell function without diminished effect on humoral (B-cell) immunity, comprising administering to a subject an effective amount of a compound of claim 1.

* * * * *

UNITED STATES PATENT AND TRADEMARK OFFICE
CERTIFICATE OF CORRECTION

PATENT NO. : 5,736,549  Page 1 of 7
DATED : April 7, 1998
INVENTOR(S) : Beasley, et al It is certified that error appears in the above-identified patent and that said Letters Patent is hereby corrected as shown below:

Cover page, ABSTRACT:

"Compounds of formula I

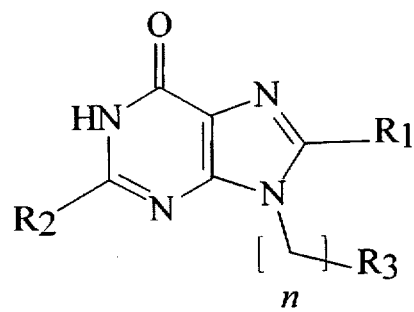

where n=0-2;

$R^1$ is H, $NH_2$ or a halogen;

$R^2$ is H or $NH_2$;

$R_3$ is any of the four groups

UNITED STATES PATENT AND TRADEMARK OFFICE
CERTIFICATE OF CORRECTION

PATENT NO. : 5,736,549
DATED : April 7, 1998
INVENTOR(S) : Beasley, et al

It is certified that error appears in the above-identified patent and that said Letters Patent is hereby corrected as shown below:

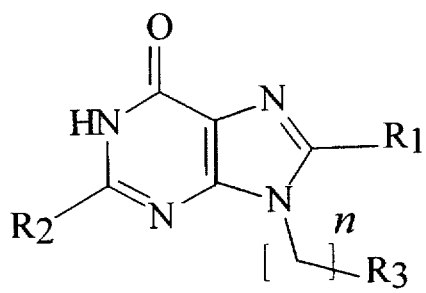

where m=0 or 1; and

X is O, $NR^5$, or $S(O)_{0-2}$ and, in group (b), the X's may be the same or different.

Compounds of the invention have utility as inhibitors of purine nucleoside phosphyorylase (PNP)."

UNITED STATES PATENT AND TRADEMARK OFFICE
CERTIFICATE OF CORRECTION

PATENT NO. : 5,736,549
DATED : April 7, 1998
INVENTOR(S) : Beasley, et al

It is certified that error appears in the above-identified patent and that said Letters Patent is hereby corrected as shown below:

Should read:

--Compounds of formula I

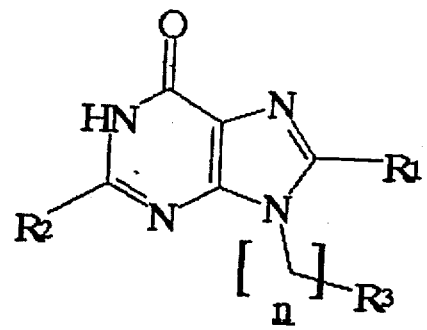

n=0-2;

$R^1$ is H, $NH_2$ or a halogen;

$R^2$ is H or $NH_2$;

$R_3$ is any of the four groups:

UNITED STATES PATENT AND TRADEMARK OFFICE
CERTIFICATE OF CORRECTION

PATENT NO. : 5,736,549
DATED : April 7, 1998
INVENTOR(S) : Beasley, et al

It is certified that error appears in the above-identified patent and that said Letters Patent is hereby corrected as shown below:

(a) 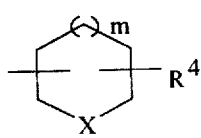   (b) 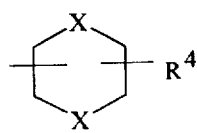

(c) 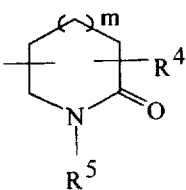   (d) 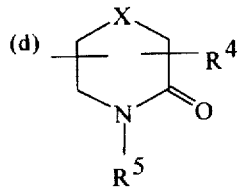

where m=0 or 1; and

X is O, $NR^5$, or $S(O)_{0-2}$ and, in group (b), the X's may be the same or different.

Compounds of the invention have utility as inhibitors of purine nucleoside phosphyorylase (PNP).--.

UNITED STATES PATENT AND TRADEMARK OFFICE
CERTIFICATE OF CORRECTION

PATENT NO. : 5,736,549
DATED : April 7, 1998
INVENTOR(S) : Beasley, et al

It is certified that error appears in the above-identified patent and that said Letters Patent is hereby corrected as shown below:

Column 25, lines 59-65, claim 1:

"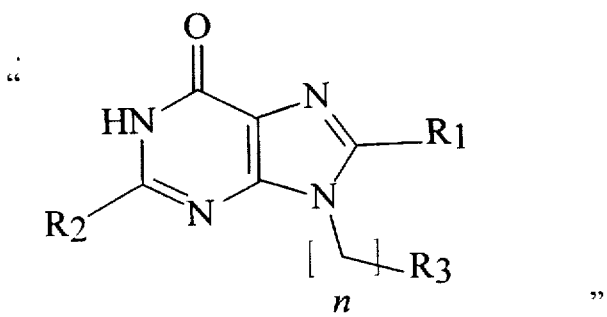"

Should read: --

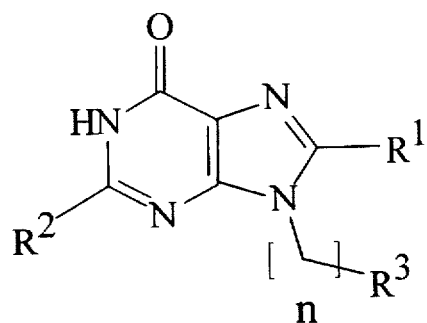

--.

UNITED STATES PATENT AND TRADEMARK OFFICE
CERTIFICATE OF CORRECTION

PATENT NO. : 5,736,549
DATED : April 7, 1998
INVENTOR(S) : Beasley, et al

It is certified that error appears in the above-identified patent and that said Letters Patent is hereby corrected as shown below:

Column 26, lines 5-12, claim 1:

"
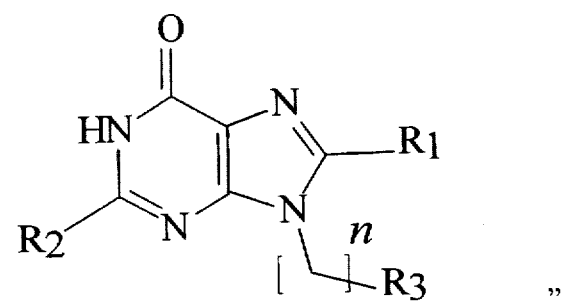
"

UNITED STATES PATENT AND TRADEMARK OFFICE
CERTIFICATE OF CORRECTION

PATENT NO. : 5,736,549
DATED : April 7, 1998
INVENTOR(S) : Beasley, et al It is certified that error appears in the above-identified patent and that said Letters Patent is hereby corrected as shown below:

Should read: -- a) 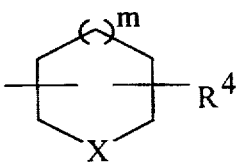  b) 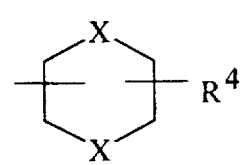

c) 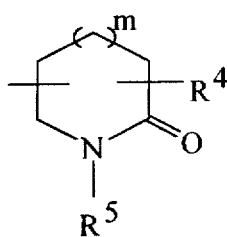  d) 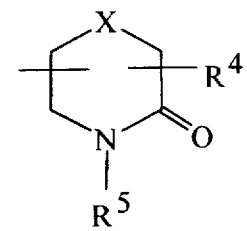

--.

Signed and Sealed this

Eighth Day of December, 1998

*Attest:*

BRUCE LEHMAN

*Attesting Officer*    Commissioner of Patents and Trademarks